United States Patent [19]

Masten

[11] Patent Number: 5,213,802

[45] Date of Patent: May 25, 1993

[54] PHARMACEUTICAL FORMULATIONS EMPLOYING ESTERIFIED ALKOXYLATED POLYOLS AS VEHICLES

[75] Inventor: Lawrence W. Masten, West Chester, Pa.

[73] Assignee: Arco Chemical Technology, L.P., Wilmington, Del.

[21] Appl. No.: 586,839

[22] Filed: Sep. 24, 1990

Related U.S. Application Data

[63] Continuation-in-part of Ser. No. 348,314, May 5, 1989, abandoned.

[51] Int. Cl.$^5$ ............................................. A61K 47/00
[52] U.S. Cl. ................................ 424/439; 424/401; 424/436; 424/441; 424/450; 514/772; 514/777; 514/785; 514/780
[58] Field of Search ............... 424/78, 439, 401, 450, 424/436, 441; 514/785, 772, 786, 777

[56] References Cited

U.S. PATENT DOCUMENTS

| | | | |
|---|---|---|---|
| 2,610,125 | 9/1952 | Valko | 99/123 |
| 2,908,681 | 10/1959 | Anderson et al. | 260/234 |
| 2,976,251 | 3/1961 | Brokaw et al. | 253/316 |
| 3,337,595 | 8/1967 | Lamont | 260/410.6 |
| 3,536,816 | 10/1970 | Kellner et al. | 424/365 |
| 3,772,446 | 11/1973 | Larsson | 424/365 |
| 4,600,539 | 7/1986 | Hoppe et al. | 260/410.7 |
| 4,687,843 | 8/1987 | Smolin et al. | 536/18.3 |
| 4,849,242 | 7/1989 | Kershner | 426/601 |
| 4,861,613 | 8/1989 | White et al. | 426/611 |

FOREIGN PATENT DOCUMENTS

| | | |
|---|---|---|
| 564516 | 10/1958 | Canada. |
| 55-79313 | 6/1980 | Japan. |
| 80-160710 | 12/1980 | Japan. |

OTHER PUBLICATIONS

Chem Abstracts 94:180500k [Japanese Kokai No. 80-160,710 (Nisshin Oil Mills)].
Funk and Wagnalls Standard College Dictionary, pp. 406 and 518 (1968).
McGraw-Hill Dictionary of Scientific and Technical Terms, Fourth Edition pp. 583 and 747 (1989).

Primary Examiner—Thurman K. Page
Assistant Examiner—Peter F. Kulkosky
Attorney, Agent, or Firm—Stephen D. Harper

[57] ABSTRACT

Pharmaceutical formulations employing novel non-allergenic, non-irritating, non-toxic, and non-digestible carriers, bases, or vehicles for topical or ingestible drug delivery are disclosed. The carriers are esterified alkoxylated polyols; preferred carrier embodiments include propoxylated glycerols which are esterified with $C_8$–$C_{24}$ fatty acids. The non-digestibility of the esterified alkoxylated polyols permits, for example, delivery of medicaments taken orally directly to the lower gastrointestinal tract.

24 Claims, No Drawings

PHARMACEUTICAL FORMULATIONS EMPLOYING ESTERIFIED ALKOXYLATED POLYOLS AS VEHICLES

This application is a continuation-in-part of application Ser. No. 07/348,314 filed May 5, 1989 now abaonded.

FIELD OF THE INVENTION

This invention relates to the use of esterified alkoxylated polyols (EAPs) as topical or ingestible carriers and vehicles for drugs. EAPs as drug vehicles have beneficial properties in that the EAPs are relatively stable and substantially non-irritating, thus allow treatment of the lower GI tract with orally administered drugs as opposed to treatment via suppositories, enemas, parenteral compositions, or the like. Likewise, the properties of the EAPs are excellent for topically administered drugs in the form of salves, creams, ointments, solutions and the like.

BACKGROUND OF THE INVENTION

Orally administered drugs are generally useful if the medication is effective when absorbed from the stomach and/or small intestine. Thus, conventional digestible carriers are useful for those medicaments. However, once the carrier is broken down by digestion, a drug cannot be delivered further. This makes treatment of the lower GI tract with orally administered drugs in standard digestible carriers substantially ineffective.

Accordingly, treatment of the large intestine and rectum is usually accomplished by anal exposure, e.g., enemas, suppositories, etc. This represents a clear disadvantage in terms of convenience to the patient.

The prior art has many examples of substances that are digestible being used as drug carriers. In particular, the use of glycerin and certain of its derivatives is known in the art.

U.S. Pat. No. 2,976,251 (Brokaw and Lyman, 1961) discloses the use of a high purity monoglyceride composition in gel form to be used as a carrier material for medicaments such as vitamins, amines, enzymes, hormones, and the like.

U.S. Pat. No. 3,536,816 (Kellner, 1970) teaches the use of a water-in-oil emulsion as a vehicle for pharmaceuticals. Kellner discloses gels, creams, and ointments for topical application to the skin.

U.S. Pat. No. 3,772,446 (Larsson, 1973) discloses an ointment base formulated with an α-monoglyceride of a $C_{12-18}$ fatty acid. This formulation is also usable for topical application.

U.S. Pat. No. 4,305,936 (Klein, 1981) discloses a ointment type medicament that utilizes a glycerol ester of a fatty acid as a carrier.

U.S. Pat. No. 4,316,902 (Yu, et al., 1982) discloses an anhydrous base for medicaments composed of isopropyl myristate or isopropyl palmitate combined with glycerol monostearate.

None of the prior art found addresses the problem of providing a drug vehicle that can carry medicaments to the lower GI tract.

It is clear that the pharmaceutical field could make significant use of carriers that are non-digestible, non-toxic, and suitable for both topical and ingestible drug delivery.

It is among the objects of this invention to provide improved pharmaceutical formulations employing non-allergenic, non-digestible, non-toxic esterified alkoxylated polyols (EAPs) as carriers, bases or vehicles.

It is another object of this invention to provide esterified propoxylated glycerols suitable for use as non-toxic, non-irritating, non-digestible, and non-allergenic carriers for medicaments.

The recitation of such objects is not limitative of the scope of the subject matter of this invention. Still further and other objects will be evident from the specification and claims of this application.

SUMMARY OF THE INVENTION

This invention provides a pharmaceutical formulation comprising an effective amount of a medication ingredient in admixture with an esterified alkoxylated polyol carrier of formula $$[BCO]_w-\overset{\overset{O}{\|}}{\underset{\underset{[O-(A)_m-C^1R^1R^2-C^2R^3R^4-OCB]_z}{|}}{P}}\overset{[OH]_x}{\underset{|}{+}}O-(A)_n-C^1R^1R^2-C^2R^3R^4-OH]_y$$

wherein (a) P is an organic radical derived from a polyol, the sum of $w+x+y+z$ is from 2 to 8,

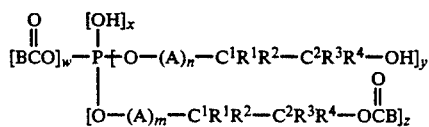

is an average number less than about 0.15, z is an average number in the range of from about 2 to the sum of $w+x+y+z$, A is an oxyalkylene unit having at least 3 carbon atoms, B is a $C_7-C_{23}$ hydrocarbon group, at least one of $R^1$, $R^2$, $R^3$, and $R^4$ is a moiety other than hydrogen, and $C^2$ is a carbon that on average is from 0 to about 5 percent primary, (b) said values of m, n, w, x, y, and z are selected to provide suitable pharmaceutical carrier properties; (c) said esterified alkoxylated polyol carrier is present in an amount sufficient to impart suitable body or coverage to said formulation; (d) said esterified alkoxylated polyol carrier is substantially dermally non-allergenic, non-irritating, non-digestible, and non-toxic; and (e) said pharmaceutical formulation is characterized by the absence of a foodstuff.

A particularly preferred embodiment of this invention provides a pharmaceutical formulation comprised of an effective amount of a medication ingredient in admixture with an esterified propoxylated glycerol carrier of formula $$[BCO]_w-\overset{\overset{O}{\|}}{\underset{\underset{[O-(A)_m-C^1R^1R^2-C^2R^3R^4-OCB]_z}{|}}{P}}\overset{[OH]_x}{\underset{|}{+}}O-(A)_n-C^1R^1R^2-C^2R^3R^4-OH]_y$$

wherein (a) P is a glyceryl radical, the sum of $w+x+y+z$ is 3,

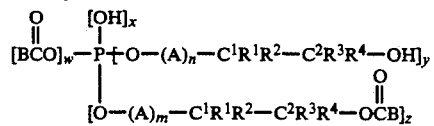

is an average number less than about 0.15, z is an average number in the range of from about 2 to 3, A is an oxypropylene unit, B is a $C_{11}-C_{21}$ hydrocarbon group, the average value of $[(m\cdot z)+(n\cdot y)]$ is from 0 to about 15, one only of $R^1$, $R^2$, $R^3$, or $R^4$ is methyl and the other R groups are hydrogen, and $C^2$ is a carbon that on average is from 0 to about 5 percent primary; (b) said values of m, n, w, x, y, and z are selected to provide suitable pharmaceutical carrier properties; (c) said esterified propoxylated glycerol carrier is present in an amount sufficient to impart suitable body or coverage to said formulation; (d) said esterified propoxylated glycerol carrier is substantially dermally non-allergenic, non-irritating, non-digestible, and non-toxic; and (e) said pharmaceutical formulation is characterized by the absence of a foodstuff.

Methods of administering one or more medication ingredients to an animal or human subject using an esterified alkoxylated polyol carrier in admixture with the medication ingredient(s) are also provided by this invention.

DETAILED DESCRIPTION OF THE INVENTION

The structure of the novel carrier of this invention may be generally represented as

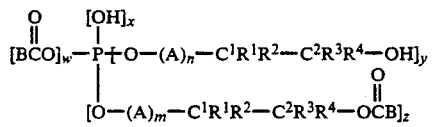

P is an organic radical derived from a polyol. In this context, the term "polyol" is intended to signify a polyhydric alcohol, i.e., one containing from two to eight hydroxyl groups. Diols, triols, tetrols, saccharides, and sugar alcohols are general classes of preferred polyols. Suitable diols are compounds having two hydroxy groups, including, but not limited to, 1,2-glycols such as ethylene glycol and propylene glycol as well as dihydroxyl compounds such as 1,3-propanediol, 1,4-butanediol, 1,5-pentanediol, 2,4-pentanediol, pinacol, and the like. Specific examples of preferred triols (compounds having three hydroxyl groups) include, but are not limited to, glycerol, trimethylol propane, trihydroxypentane, trihydroxyhexane, and their mixtures. Examples of suitable tetrols include erythritol and pentaerythritol. Suitable saccharides include, for example, glucose, fructose, mannose, galactose, arabinose, xylose, sorbose, sucrose, sorbitol and the like. Also suitable are the sugar alcohols corresponding to the general formula $HOCH_2(CHOH)_nCH_2OH$, where $n=2-6$. The preferred polyol is glycerol.

Mixtures of diols, triols, sugar alcohols, and saccharides may be used. Other polyols having from 2 to 8 hydroxyl groups are also suitable.

In the esterified alkoxylated polyols of this invention, A is an oxyalkylene unit derived from an epoxide containing at least 3 carbon atoms. Epoxides containing from 3 to 6 carbon atoms are preferred. Examples of suitable epoxides include, but are not limited to, propylene oxide, 1,2-pentene oxide, trimethylethylene oxide, 1,2-butene oxide, tetramethylethylene oxide, styrene oxide, 2,3-butene oxide, allyl glycidyl ether, phenyl glycidyl ether, epichlorohydrin, cyclohexene oxide, and isobutylene oxide. Propylene oxide is the preferred epoxide. It is preferred that the average value of $[(m \cdot z)+(n \cdot y)]$ be in the range of from 0 to about 15. More preferably, this value is in the range of from about 0.67 to about 11. The degree of alkoxylation is preferably such that the rate of porcine pancreatic lipase hydrolysis is less than about 20%, more preferably less than about 10%, relative to olive oil.

The ester groups

in the esterified alkoxylate polyols are derived from long chain $C_8-C_{24}$ fatty acids. B is thus a $C_7-C_{23}$ hydrocarbon group; more preferably, B is a $C_{13-21}$ paraffinic or olefinic hydrocarbon group. Examples of suitable $C_{8-24}$ fatty acids include caprylic, capric, lauric, myristic, myristoleic, stearic, palmitic, palmitoleic, rincinoleic, linoleic, linolenic, elaeostearic, arachidic, behenic, erucic, oleic, and heptadecanoic acid. The physical properties of the EAP may be varied as desired by changing the length and structure of hydrocarbon group B; products which are liquid oils, fats, greases, or solid waxes may thus be obtained. The fatty acid chain length is also believed to contribute to the non-digestible properties of the esterified alkoxylated polyol by making the EAP non-absorbable in the digestive tract. The fatty acids can be either synthetic or naturally occurring fatty acids and may be either saturated or unsaturated. For example, rapeseed oil provides a good source for $C_{22}$ acid ($B=C_{21}$). $C_{16}-C_{18}$ fatty acids ($B=C_{15-17}$) can be obtained from tallow, soybean oil, or cottonseed oil. Shorter chain fatty acids can be provided by coconut, palm kernel oil, or babassu oils. Corn oil, fish oil lard, olive oil, palm oil, peanut oil, safflower seed oil, sesame seed oil, jojoba oil and sunflower seed oil are examples of other natural oils which can serve as the source of the fatty acid component. Among the fatty acids, those that are preferred have from about 14 to about 22 carbon atoms ($B=C_{13-21}$), and are most preferably selected from the group consisting of myristic, palmitic, stearic, oleic, behenic, and linoleic. The preferred sources for the fatty acid components are natural fats and oils which have a high content of these fatty acids, e.g., soybean oil, rapeseed oil, olive oil, cottonseed oil, corn oil, tallow and lard.

The carbon connected to the ester group

in the esterified alkoxylated polyol is preferably from about 85 to 100% secondary and/or tertiary on average in order for the EAP to be substantially non-digestible in the digestive tract. In other words, $C^2$ in the general formula given for the esterified alkoxylated polyol carrier of this invention generally is preferred to be from about 0 to about 15 percent primary on average. Most, preferably, the relative proportion of primary $C^2$ is from 0 to about 5 percent. Without wishing to be bound by theory, it is believed that the non-digestibility of the EAP carrier of this invention is due to at least some extent to the absence of substantial proportions of primary

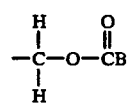

linkages. The esters of tertiary alcohols (i.e., where $R_3$ and $R_4$ are both moieties other than hydrogen) or secondary alcohols (i.e., where $R_3$ is a moiety other than hydrogen and $R_4$ is hydrogen) appear to provide good protection against lipase hydrolysis. When $R^1R^2$, $R^3$, or $R^4$ are groups other than hydrogen, they may be any moiety which effectively blocks hydrolysis of the ester group in the digestive tract. Such moieties include, for example, alkyl groups such as methyl, ethyl, and propyl, aryl groups such as phenyl, alkyl ether groups such as —$CH_2OR$ where R is phenyl, alkyl, allyl, etc., and haloalkyl groups such as —$C_2X$ where X is Cl, Br, etc. $R^1$, $R^2$, $R^3$, and $R^4$ may be the same or different.

In order for the esterified alkoxylated polyol to be substantially non-allergenic, non-irritating, as well as non-digestible, non-absorbable, and non-toxic in the digestive tract, $$\frac{x+y}{w+x+y+z}$$

generally should be relatively low and preferably below about 0.15. Most preferably, $$\frac{x+y}{w+x+y+z}$$

is below about 0.05. In other words, it is advantageous that the alkoxylated polyol be completely or nearly completely esterified and that the proportion of hydroxyl groups (x+y) is low relative to the proportion of ester groups (w+z) in the final EAP product. This may be determined experimentally by measurement of the hydroxyl number of the esterified alkoxylated polyol.

Particularly preferred embodiments of the pharmaceutical formulations of this invention include an effective amount of a medication ingredient in admixture with an esterified propoxylated glycerol carrier of formula

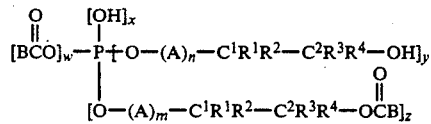

wherein P is a glyceryl radical, the sum of w+x+y+z is 3, $$\frac{x+y}{w+x+y+z}$$

is an average number less than about 0.05, z is an average number in the range of from about 2 to 3, A is an oxypropylene unit, the average value of [(m·z)+(n·y)] is from 0 to about 15, B is a $C_{11}$-$C_{21}$ hydrocarbon group, and only one of $R^1$, $R^2$, $R^3$, and $R^4$ is methyl with the other R groups being hydrogen, provided that on average $C^2$ is from 0 to about 5 percent primary. In an especially preferred embodiment of the invention, w, x, and y are essentially 0 and the structure of the resulting esterified propoxylated glycerol may be represented as being predominantly

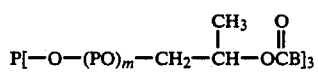

where PO represents an oxypropylene unit.

Even when the preferred esterified propoxylated glycerols (EPGs) of this invention are deliberately hydrolyzed, no outward sign of toxicity of the resulting alkoxylated polyols is observed. Propylene glycol, which would be released if the EPG ether linkage were to be cleaved, is given GRAS (Generally Recognized As Safe) status by the U.S. Food and Drug Administration. Propylene glycol and its derivatives are used at low levels in the food industry, e.g., as solvents for flavors and pharmaceuticals, and in baked goods, salad dressings and sauces.

The EAPs useful as carriers in the pharmaceutical formulations of this invention possess the additional advantage of having little or no taste or odor. Thus, the pharmaceutical formulations are expected to be readily acceptable to consumers due to the absence of unpleasant or disagreeable flavor or smell.

The esterified alkoxylated polyols useful as carrier ingredients in the pharmaceutical formulations of this invention may be prepared by any suitable method. A general synthetic route to the EAPs involves first alkoxylating a starting polyol such as a diol, triol, saccharide, or sugar alcohol with the desired number of equivalents of epoxide to form an alkoxylated polyol and then esterifying the hydroxy groups of the alkoxylated polyol intermediate using one or more fatty acids or fatty acid derivatives.

The alkoxylation is preferably performed under base-catalyzed conditions using, for example, an alkali metal catalyst such as potassium hydroxide. This approach has the advantage of forming predominantly secondary or tertiary hydroxy end-groups on the alkoxylated polyol intermediate, since nucleophilic attack of the alkoxide end-group of the alkoxylated polyol intermediate tends to occur at the least substituted carbon of the epoxide. For example, base-catalyzed alkoxylation of a polyol using propylene oxide as the epoxide gives about 98% secondary and only about 2% primary hydroxyl end-groups [Gibson, et al *J. Appl. Polymer Sci.* 14, 1059 (1970)]. As mentioned previously, it is desirable for reasons of non-digestibility that the carbon which is ultimately attached to the ester group in the final EAP (corresponding to the terminal carbon of the alkoxylated polyol intermediate) be at least about 85 percent secondary and/or tertiary on average.

The esterification of the intermediate alkoxylated polyol may be accomplished using any suitable method known for synthetic transformations of this type. For example, a fatty acid or mixture of fatty acids may be reacted with the alkoxylated polyol to yield the EAP and water as a by-product. A catalyst may be used, preferably an acidic catalyst such as a mineral acid (sulfuric acid, for example) or a sulphonic acid (p-toluene sulphonic acid, for example). Alternatively, a transesterification reaction may be employed wherein a fatty acid ester

or mixture of fatty acid esters is reacted with the alkoxylated polyol. Preferably, the fatty acid ester contains a low boiling alcohol moiety (R=$CH_3$, for example) which may be removed from the transesterification reaction mixture in order to drive the equilibrium reaction to completion in the desired direction. A catalyst may be used in the transesterification. In yet another approach, the alkoxylated polyol may be reacted with an acid halide derivative of one or more fatty acids

[XCB, where X=Cl, Br, etc.,]. A base such as a tertiary amine may be added to remove the HX generated.

It should be understood that by the nature of the chemical reactions used to prepare the esterified alkoxylated polyols, the products obtained will generally be mixtures of individual compounds which have a range of molecular weights and which may contain structural isomers. It may be useful to deliberately blend individually prepared EAPs having different degrees of alkoxylation, different functionality (the sum of w+x+y+z), and/or different B substituents in order to obtain pharmaceutical carriers having certain desired properties.

The esterified alkoxylated polyol may be combined with an effective amount of any suitable medication ingredient to give the novel pharmaceutical formulations of this invention. Depending upon the physical and medicinal characteristics of the formulation which are desired, the amount of the esterified alkoxylated polyol carrier can range from 0.1 to 99.9 weight percent. The esterified alkoxylated polyol can be used in combination with other carriers. The medication ingredient should be present in an amount sufficient to effect the desired medicinal result. In this context, medication ingredient is defined as a substance other than food intended for use in the diagnosis, cure, mitigation, treatment, or prevention of disease in man or other animal or intended to affect the structure or function of the body of man or other animal. The pharmaceutical formulations of this invention are thus characterized by the absence of a foodstuff (i.e., a material containing carbohydrates, fats, proteins, or supplementary substances such as vitamins or minerals that is taken or absorbed into the body of an organism in order to sustain growth and all vital processes and to furnish energy for all activity of the organism).

Examples of suitable medicaments include, but are not limited to, analgesics, anti-inflammatory agents, ganglionic blocking agents, sympathetic blocking drugs such as beta blocking drugs, anesthetics, vaccines, serums, parasympathomimetic drugs, anti-pyretics, appetite-suppressants, cardiovascular agents, chemotherapeutics, contraceptive drugs, antiseptics, diuretics, hormones, expectorants, anti-tussives, gastrointestinal agents, anti-histamines, laxatives, insulin and other anti-diabetic agents, hypnotics, narcotics, tranquilizers, sedatives, anti-convulsants, immunotherapeutic agents, memory-enhancing agents, anti-aging drugs, neuroregulators, prostaglandins, psychopharmacological agents, steroids, and thyroid preparations. The pharmaceutical formulations of this invention are suitable for use for the treatment of human as well as animal subjects.

Esterified alkoxylated polyols may also be used as components in the preparation of liposomes. Liposomes are extremely small spheres comprised of a fatty carrier and a medication ingredient which are useful for the slow release or specific delivery of the medication ingredient within the body. There has long been a need in the art for liposomes which are more resistant to digestion. Microphages in the blood stream, for example, often consume conventional liposomes before they can reach targeted areas of the body. The non-digestible and non-toxic nature of the esterified alkoxylated polyols make such substances ideally suited for use in liposome applications.

The following detailed description illustrates the invention by way of example, not by way of limitation of the principles of the invention. This description will clearly enable one skilled in the art to make and use the invention, and describes several embodiments, adaptations, variations, alternatives and uses of the invention, including what I presently believe is the best mode of carrying out the invention.

In one embodiment, the oxyalkylene unit A is represented by oxypropylene (PO), the polyol P by glyceryl (G), and the fatty acid ester moiety

by a mixture of either palmitic and oleic acid or heptadecanoic and oleic acid. The esterified propoxylated glycerol (EPG) thus corresponds to the formula

where n is an average number in the range of from 2 to 18. With the addition of 5 PO units (n=5), nearly all of the hydroxyl groups of the original glycerol will have been propoxylated. The best mode embodiment contemplated employs an EPG with, on average, 5–18 moles of propylene oxide per mole of glycerin and esterified with oleic acid, stearic acid, or similar long chain fatty acids.

EXAMPLES

I. Synthesis of EAPs

For the synthesis of the propoxylated glycerols and the esterified propoxylated glycerols, the method of U.S. Pat. No. 4,861,613 was followed. The disclosure of that patent is hereby incorporated by reference.

II. In Vitro Testing of the EPGs (n=1–14) for Digestion by Porcine Pancreatic Lipase Following the procedure in the above referenced U.S. Pat. No. 4,861,613, EPGs of general formula

were prepared in which n was varied in the range of from 1–14 by control of the amount of PO in the propoxylation reaction. 100 mg of each EPG to be tested was added to 10 ml of buffer containing 1 mM NaCl, 1 mM CaCl$_2$, 3 mM deoxycholate, 2 mM tris(hydroxymethyl) amino methane, and 10 g/l of gum arabic. The mixtures were vigorously shaken in capped test-tubes, and the emulsions transferred to the pH stat reaction vessel. The pH was titrated to 8.0 using a radiometer pH stat (comprising a TTA80 titration assembly, a TTT80 titrator, and ABU80 autoburette and a pHM82 pH meter). Porcine pancreatic lipase (0.1 ml, equivalent to 1000 units of enzyme, at pH 8.0) was added, the pH rapidly re-equilibrated to 8.0, and then the reaction followed over a 20 minute period by autotitration with 50 mM aqueous NaOH. The initial, linear rate is reported as micromoles of NaOH per hour required to keep the pH constant by neutralizing the free fatty acids released by the action of pancreatic lipase.

The results obtained are given below in Table I, expressed as an average of 4 determinations relative to olive oil as a control (100%), where the

ester moiety is derived from a 1:5 molar mixture of either palmitic acid and oleic acid or heptadecanoic acid and oleic acid.

TABLE I

| Digestibility (Lipase Activity) | |
|---|---|
| Substrate | Relative Rate* |
| Control: Olive Oil | 100 |
| Invention EPGs: $G(PO)_n(OCB)_b$ | |
| n = 0 | 76.2 |
| n = 1 | 46.2 |
| n = 2.2 | 18.9 |
| n = 5 | 0 |
| n = 8 | 0 |
| n = 14 | 0 |

*Average of four determinations.

Based on the above Table I data, at n=3 the lipase hydrolysis rate is about 10%, and at n=4 it is about 5%. It is preferred that the lipase hydrolysis rate be below about 20%; more preferably, the rate is less than about 10%.

The corresponding acetate adducts of the tested EPGs of Table I (n=1, 2.2, 5, 8 and 14) were assayed by Gas Liquid Chromatography (packed column) to show the distribution of polypropylene oxide units in each. The results are shown in Table II.

TABLE II

| Adduct | DISTRIBUTION OF POLYEPOXIDE UNITS % AREA BY GLC (PACKED COLUMN) | | | | | | | | | | | |
|---|---|---|---|---|---|---|---|---|---|---|---|---|
| | PG | G | 1:1 | 1:2 | 1:3 | 1:4 | 1:5 | 1:6 | 1:7 | 1:8 | 1:9 | 1:10 |
| $G(PO)_1$ | ND | 31.1 | 46.2 | 19.9 | 2.7 | | | | | | | |
| $G(PO)_{2.2}$ | ND | 2.1 | 22.7 | 40.5 | 28.0 | 5.9 | 0.7 | | | | | |
| $G(PO)_5$ | t | ND | ND | 1.4 | 16.1 | 34.5 | 28.5 | 13.6 | 5.1 | 0.8 | | |
| $G(PO)_8$ | t | ND | ND | ND | 4.9 | 13.3 | 22.3 | 25.8 | 22.6 | 8.3 | 2.7 | ND |

ND = Not detectable
t = trace
PG = propylene glycol
G = glycerin

The above components represent 90% of the mass trace integral, except for $G(PO)_8$ where the value was 67.8% due to presence of unknown additional component (NOT triacetin). The area % was not corrected to give mass or mole % (FID response factors unknown).

III. Four Week Feeding Study in Rats

A four week feeding study was conducted which was designed to evaluate the short term oral safety of four different esterified propoxylated glycerols and their effect on fat disposition in the gastrointestinal (GI) tract. Two different levels of propoxylation (n TM 8 and n=14) and three different fatty acid sources (oleate, stearate, and soyate) were employed. The four are designated as EPG-08 oleate, EPG-14 oleate, EPG-08 stearate, and EPG-08 soyate.

Male Charles River SD rats were fed these materials ad libitum in the diet. Each group of ten animals received 5% EPG plus 2% corn oil in a semisynthetic fat-free diet while a control group was fed 7% corn oil in the same fat-free diet.

The animals were observed twice daily for signs of toxic effects. Body weights (weekly), food consumption data (three times weekly), and 24-hour fecal dry weights (three times weekly) were determined and recorded. Fecal fat levels were estimated from the feces collected. Selected hematology (16) and clinical chemistry (18) parameters were performed on blood collected at the terminal sacrifice. Additionally, during the necropsy that followed, the animals were examined macroscopically, selected organs were weighed and tissues and organs were collected. A wide range of tissues (30) were evaluated histopathologically from all animals in the EPG-08 soyate group and compared to those of the corn oil group.

All animals remained healthy throughout the feeding study. There were no statistically significant treatment related changes observed in the body weights or food intake of the EPG groups compared to the corn oil controls, although body weight tended to be lower than in the control group with the sole exception of the EPG-08 soyate group. In general, it was noted that food intake in the EPG groups was approximately 3–7% greater than the control group. Thus, the EPG groups apparently ate more to compensate for the lower caloric content of their diets.

Fecal fat levels in all the groups receiving EPG were greatly elevated (5- to 8-fold) when compared to the corn oil group, indicating a lack of absorption of these test materials.

No treatment related findings were observed in any of the hematological or clinical chemistry parameters monitored in the EPG groups. Nor were there any changes noted in the macroscopic appearance of organs and tissues examined from these animals. All organ weights were unaffected by the EPG diets. A histopathologic evaluation of animals from the EPG-08 soyate group failed to reveal any difference from that of the corn oil control group.

These results support the likelihood that little or no esterified propoxylated glycerol is "digested" when consumed. Since triglycerides are known not be absorbed as such from the GI tract unless digested to at least mono- and diglycerides, and fatty acids, the EPGs tested probably were not absorbed as a result of their resistance to digestion.

IV. Testing for Skin and/or Eye Irritation

In addition to its non-digestibility, a major advantage of an EAP over a conventional pharmaceutical base is the fact that EAPs exhibit little or no dermal or eye irritation characteristics. The studies reported below show the lack of significant irritation when an EAP was applied to the skin and eyes of test animals. The testing was performed on an EAP of the formula

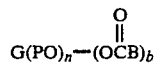

in which G is glyceryl, PO is propylene oxide,

is an oleic acid ester moiety, b is an average number between 2 and 3, and n=8 (identified as EAP-1 below). The study was conducted in accordance with Good Laboratory Practice Standards (21 CFR 58). The following is a summary of the results of the studies.

A: Primary Skin Irritation in Rabbits (Draize Method)

Skin irritation was evaluated by applying 0.5 ml of EAP-1 to 1"×1" gauze pads that were then secured to various skin sites on the test animals. (The test animals were six New Zealand White rabbits, three males and three females). The pads were held in contact with the ski site for 24 hours. Both intact and slightly abraded skin sites were evaluated immediately after the application period (24 hours) and again two days later (72 hours). The sites were scored for erythema (redness) and edema (swelling) according to the following scale:

| Scale 1: Scoring Key for Skin Reactions for Primary Irritation in Rabbits | |
|---|---|
| Skin Reaction | Score |
| Erythema: | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Edema formation: | |
| No edema | 0 |
| Very slight edema (barely perceptible) | 1 |
| Slight edema (edges of area well defined by | 2 |

| Scale 1: Scoring Key for Skin Reactions for Primary Irritation in Rabbits (continued) | |
|---|---|
| Skin Reaction | Score |
| definite raising) | |
| Moderate edema (raised approximately 1 millimeter) | 3 |
| Severe edema (raised more than 1 millimeter and extending beyond the area of exposure) | 4 |

Table III shows the results of the testing.

TABLE III

Primary Skin Irritation in Rabbits Following a 24-hour Dermal Application of EAP-1

| Skin Condition Score | Observation Time (hours) | Score for each Rabbit | | | | | | Total Score | Average |
|---|---|---|---|---|---|---|---|---|---|
| | | No. 1 | No. 2 | No. 3 | No. 4 | No. 5 | No. 6 | | |
| ERYTHEMA FORMATION | | | | | | | | | |
| | Site | C | D | A | B | C | D | | |
| Intact | 24 | 0 | 1 | 2S | 1 | 2 | 2 | 8 | 1.33 |
| | 72 | 0 | 1 | 1S | 0 | 1 | 1 | 4 | 0.67 |
| | Site | D | A | B | C | D | A | | |
| Abraded | 24 | 0 | 1 | 2S | 1 | 1 | 2S | 7 | 1.17 |
| | 72 | 0 | 1 | 1S | 1 | 1 | 1S | 5 | 0.83 |
| EDEMA FORMATION | | | | | | | | | |
| | Site | C | D | A | B | C | D | | |
| Intact | 24 | 0 | 1 | 0 | 0 | 0 | 0 | 1 | 0.17 |
| | 72 | 0 | 0 | 0 | 0 | 0 | 0 | 0 | 0.00 |
| | Site | D | A | B | C | D | A | | |
| Abraded | 24 | 0 | 0 | 0 | 0 | 0 | 0 | 0 | 0.00 |
| | 72 | 0 | 0 | 0 | 0 | 0 | 0 | 0 | 0.00 |
| | | | | | | | Primary Irritation Index | | 1.0 |

S = Erythema spreading beyond patch site.

The Primary Irritation Index (PII) is derived by summing the average scores and dividing by four. The test results are given in Table III. In this test, minimal erythema and almost no edema were found. These results indicate that the EAP-1 is not corrosive (no tissue damage), and that it is not a primary irritant when applied dermally.

B. Primary Eye Irritation in Rabbits (Draize Method)

Again, six New Zealand White Rabbits (three males and three females) were exposed to EAP-1. None of the animals used for the skin irritation test were used in this study. A small amount of EAP-1 (0.1 ml) was applied to the right eye of each of the test subjects.

Examinations for gross signs of eye irritation were made at 24, 48, and 72 hours following application. Scoring of the irritative effects was done according to the scale below:

| Scale 2: Scoring Key for Ocular Reactions for Primary Eye Irritation in Rabbits | |
|---|---|
| Ocular Reactions | Score |
| (1) Cornea | |
| (a) Opacity - degree of density (area most dense taken for reading) | |
| No Opacity | 0 |
| Scattered or diffuse area, details of iris clearly visible (mild cornea opacity) | 1 |
| Easily discernible translucent areas, details of iris slightly obscured (moderate) | 2 |
| Opalescent areas, no details of iris visible, size of pupil barely discernible (severe) | 3 |
| Opaque, iris invisible (extreme) | 4 |
| (b) Area of cornea involved | |
| One quarter (or less) but not zero | 1 |
| Greater than one quarter, but less than half | 2 |

-continued

| Scale 2: Scoring Key for Ocular Reactions for Primary Eye Irritation in Rabbits | |
|---|---|
| Ocular Reactions | Score |
| Greater than half, but less than three quarters | 3 |
| Greater than three quarters, up to whole area | 4 |
| Score = a × b × 5    Total Maximum = | 80 |
| (2) Iris | |
| (a) Values | |
| Normal | 0 |
| Folds above normal, congestion, swelling, circumcorneal injection (any or all of these or combination of any thereof) iris still reacting to light (sluggish reaction is positive) (mild iritis) | 1 |
| No reaction to light, hemorrhage, gross destruction (any or all of these) (severe iritis) | 2 |
| Score = a × 5    Total Maximum = | 10 |
| (3) Conjunctivae | |
| (a) Redness (refers to palpebral and bulbar conjunctivae excluding cornea and iris) | |
| Vessels normal | 0 |
| Vessels definitely infected above normal (slight, mild) | 1 |
| More diffuse, deeper crimson red, individual vessels not easily discernible (moderate) | 2 |
| Diffuse beefy red (severe) | 3 |
| (b) Chemosis | |
| No swelling | 0 |
| Any swelling above normal (includes nictitating membrane) (slight) | 1 |
| Obvious swelling with partial eversion of lids (moderate) | 2 |
| Swelling with lids about half closed (severe) | 3 |
| Swelling with lids about half closed to completely closed (extreme) | 4 |
| (c) Discharge | |
| No discharge | 0 |
| Any amount different from normal (does not include small amounts observed in inner can thus of normal animals (mild or slight) | 1 |
| Discharge with moistening of the lids and hairs just adjacent to lids (moderate) | 2 |
| Discharge with moistening of the lids and hairs, and considerable area around the eye (severe) | 3 |
| Score = (a + b + c) × 2    Total Maximum = | 20 |

The individual scores are then summed for a total score with a value of 0–110. The results of the testing are shown in Table IV.

TABLE IV

Primary Eye Irritation in Rabbits Following an Ocular Application of EAP-1

| Ocular Lesion | Observation Time (hours) | Score for each Rabbit | | | | | |
|---|---|---|---|---|---|---|---|
| | | No. 1 | No. 2 | No. 3 | No. 4 | No. 5 | No. 6 |
| Cornea Lesions | | | | | | | |
| Opacity Degree | 24 | 0 | 0 | 0 | 0 | 0 | 0 |
| | 48 | 0 | 0 | 0 | 0 | 0 | 0 |
| | 72 | 0 | 0 | 0 | 0 | 0 | 0 |
| Opacity Area | 24 | 0 | 0 | 0 | 0 | 0 | 0 |
| | 48 | 0 | 0 | 0 | 0 | 0 | 0 |
| | 72 | 0 | 0 | 0 | 0 | 0 | 0 |
| Iris Changes | | | | | | | |
| Iritis | 24 | 0 | 0 | 0 | 0 | 0 | 0 |
| | 48 | 0 | 0 | 0 | 0 | 0 | 0 |
| | 72 | 0 | 0 | 0 | 0 | 0 | 0 |
| Conjunctival Changes | | | | | | | |
| Erythema | 24 | 0 | 0 | 0 | 0 | 0 | 0 |
| | 48 | 0 | 0 | 0 | 0 | 0 | 0 |
| | 72 | 0 | 0 | 0 | 0 | 0 | 0 |
| Swelling | 24 | 0 | 0 | 0 | 0 | 0 | 0 |
| | 48 | 0 | 0 | 0 | 0 | 0 | 0 |
| | 72 | 0 | 0 | 0 | 0 | 0 | 0 |
| Discharge | 24 | 0 | 0 | 0 | 0 | 0 | 0 |
| | 48 | 0 | 0 | 0 | 0 | 0 | 0 |
| | 72 | 0 | 0 | 0 | 0 | 0 | 0 |
| Total Score | | | | | | | |

TABLE IV-continued

Primary Eye Irritation in Rabbits Following an Ocular Application of EAP-1

| Ocular Lesion | Observation Time (hours) | Score for each Rabbit | | | | | |
|---|---|---|---|---|---|---|---|
| | | No. 1 | No. 2 | No. 3 | No. 4 | No. 5 | No. 6 |
| | 24 | 0 | 0 | 0 | 0 | 0 | 0 |
| | 48 | 0 | 0 | 0 | 0 | 0 | 0 |
| | 72 | 0 | 0 | 0 | 0 | 0 | 0 |

The test is considered to have produced a positive result if reading of 1 or greater is exhibited in corneal opacity or iris changes, or if a reading of 2 or greater is obtained in conjunctual erythema or edema.

The material being tested is then classified according to the number of test subjects that have shown a positive result. If positive results are shown in 4–6 animals, the substance is an irritant; 2–3 animals indicates that additional testing is required; and 0–1 animals showing positive results indicates that the substance is a non-irritant.

None of the six rabbits tested showed evidence of any adverse reaction of its eye to EAP-1. Accordingly, EAP-1 is classified as a non-irritant by ocular application.

C. Guinea Pig Maximization Test (Magnusson and Kligman Method)

The potential of EAP-1 to produce delayed contact hypersensitivity in guinea pigs was evaluated by the Magnusson and Kligman Maximization Test Method.

On day zero, twenty Hartley albino guinea pigs plus ten positive control animals, and ten vehicle control animals each received six intradermal injections, i.e. duplicate injections (0.1 ml/injection) for each of the three test groups: test material (undiluted), formaldehyde (a positive dermal sensitizer; 5.0% w/v in distilled water) and acetone, respectively. Each animal also received two intradermal injections of 50% v/v Freund's Complete Adjuvant (FCA) in distilled water and two injections of the respective test or control materials in the FCA/distilled water emulsion.

On day 6, these same groups of animals were exposed topically to a preparation of their respective test (50% w/v in acetone) or control material under "ELASTOPLAST" (a product of Beiersdorf, Inc.) bandage wrappings for approximately 48 hours.

On day 19, all animals were topically challenged at a naive (not previously exposed) skin site using a preparation of their respective test or control material under "ELASTOPLAST" bandage wrappings for approximately 24 hours. Naive control animals were patched identically to and concurrently with the test and positive.

On the day after removal, the sites were depilated. Later that day and again on the next day, the sites were graded for erythema (redness).

On day 27, all of the original test animals were topically rechallenged at the naive skin site using a preparation of the material under "ELASTOPLAST" bandage wrappings for approximately 24 hours. Naive control animals were patched identically to and concurrently with the test animals.

On the day after removal, the sites were depilated. Later that day and again the next day, the sites were graded for erythema.

Following the primary challenge, the incidence of grade 1 responses was 0% in both the test group (0/20) and in the naive test control group (0.10). Due to a higher incidence of ±reactions in the test group (15/20) as compared to the naive test control group (3/10), a rechallenge was performed to determine whether this was a mere chance response or it may indicate a low level of sensitization potential.

Following the primary challenge with the positive control groups, the incidence of grade 1 responses or greater in the positive control group was 100% (10/10). The incidence of these responses was more pronounced than that produced by the naive positive control group (0.10) and resulted in a classification of extreme sensitization.

Eight days following the primary challenge application, a rechallenge with EAP-1 using a single patch was conducted with the twenty test animals. Ten naive control animals were patched identically and concurrently with the test animals. On the day after the removal, the sites were depilated. Later that day and again the next day the sites were graded for erythema.

Following the single patch rechallenge, the incidence of grade 1 responses in the test group (0.20) and the naive control group (0.10) was 0%. The incidence of ± reactions in each group remained unchanged.

Based on the results of this study, EAP-1 failed to exhibit any dermal sensitization potential. Given the fact that this type of test is the best predictor available for human dermal sensitizers and non-sensitizers with the lowest incidence of false negatives and false positives, it is highly unlikely that EAP-1 has any potential to induce dermal sensitization in humans.

V. Drug Formulations

In the examples below, the amounts indicated are percent by weight, unless otherwise indicated. Components that vary to suit the user or shelf life requirements, such as fragrances, colorants, preservatives, flavorings, etc. are indicated by "gs", meaning an amount sufficient to function in the manner intended was used. Selection of the amounts of such components is within the skill of the ordinary pharmaceutical chemist. EAP in the examples below means one or more of the esterified alkoxylated polyols of this invention, used alone or as a blend. The compositions are mixed to uniform consistency suitable for use. The consistency and amount of EAP carrier may be varied to give the required body (relative stiffness; e.g. as in a suppository) and coverage (as in a topical ointment or salve). Mixtures of EAPs and conventional carriers may also be employed if desired.

EXAMPLE 1

| Oral Preparation for Pain Reliever | |
|---|---|
| Acetaminophen | 500 mg |
| EAP Carrier | 1 gram |

EXAMPLE 2

| Hemorrhoidal Suppository | |
|---|---|
| Live Yeast Cell Derivative | 2000 Units/oz. Base* |
| Shark liver oil | 3% |
| Phenylmercuric nitrate | .01% |
| EAP Carrier | 8 grams |

*(2000 Units skin respiratory factor/oz. of base

EXAMPLE 3

| Oral Preparation for Diarrhea Relief | |
|---|---|
| Kaolin | 90 grams |
| Pectin | 2 grams |
| EAP Carrier | 50 grams |

EXAMPLE 4

| Chewable Cough Suppressant | |
|---|---|
| Dextromethorphan hydrobromide | 15 mg |
| EAP Base | 15-30 grams |

EXAMPLE 5

| Antibacterial Salve | |
|---|---|
| Polymyoxin B Sulfate | 10,000 units |
| Neomycin Sulfate Equivalent | 3.5 mg |
| Methyl Paraben | .25% |
| EAP Carrier | 1 gram |

EXAMPLE 6

| Topical Skin Cream | |
|---|---|
| (Useful as an anti-irritant for rashes & itching caused by eczema, dermatitis, detergents, poison ivy, oak & sumac, insect bites, genital & rectal itching). | |
| Hydrocortisone Acetate | 0.5% |
| EAP Carrier (Cream Consistency) | 99.5% |

EXAMPLE 7

| Pain Relieving Ointment | |
|---|---|
| (Useful for minor arthritis pain and muscle ache). | |
| Methyl salicylate | 1-15% |
| Menthol | gs to 5% |
| EAP Carrier | balance |

EXAMPLE 8

| Antiseptic Ointment | |
|---|---|
| Boric Acid | 10% |
| EAP Carrier | 90% |

EXAMPLE 9

| Liposomal Preparation For Oral Treatment of Lower Bowel Inflammation | |
|---|---|
| EAP Carrier | 1 gram |

| Liposomal Preparation For Oral Treatment of Lower Bowel Inflammation | |
| --- | --- |
| Hydrocortisone Acetate | 20 milligrams |

Sonicate mixture in aqueous medium to desired liposomal preparation with average liposomal diameter of 1-10 microns.

EXAMPLE 10

| Liposomal Preparation For Oral Treatment of Lower Bowel Infection | |
| --- | --- |
| EAP Carrier | 1 gram |
| Tetracycline Hydrochloride | 250 milligrams |

Sonicate mixture in aqueous medium to desired liposomal preparation with average diameter of 1-10 microns.

Tetracycline Hydrochloride 250 milligrams Sonicate mixture in aqueous medium to desired liposomal preparation with average diameter of 1-10 microns.

The data preceding the examples show that EAPs are useful as vehicles or carriers for drugs which may be dissolved, suspended, and/or emulsified in the EAP.

Due to their lack of absorption from the GI tract, EAPs decrease the absorption of the drug from the small intestine and protect the drug from degradation due to hydrolysis and other types of metabolic activity. Likewise the non-allergenic, non-irritability and non-toxic properties of the EAP carriers permit their use in topical drug delivery applications.

Accordingly, the use of EAPs as pharmaceutical vehicles promotes the transit of a drug to the stomach and GI tract, particularly the lower end of the GI tract. This allows medication taken orally to be delivered to the lower GI tract more beneficially and conveniently than other delivery systems (e.g. suppositories, enemas, and systemic delivery following general absorption).

It should be understood that various modifications within the scope of this invention can be made by one of ordinary skill in the art without departing from the spirit thereof. I therefore wish my invention to be defined by the scope of the appended claims as broadly as the prior art will permit, and in view of this specification if need be.

I claim:

1. An improved pharmaceutical formulation comprising an effective amount of a medication ingredient in admixture with an esterified alkoxylated polyol carrier of formula

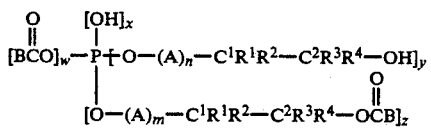

wherein
(a) P is an organic radical derived from a polyol, the sum of $w+x+y+z$ is from 2 to 8, $$\frac{x+y}{w+x+y+z}$$

is an average number in the range of from 0 to about 0.15, z is an average number in the range of from about 2 to the sum of $w+x+y+z$, A is an oxyalkylene unit having at least 3 carbon atoms, B is a $C_7$-$C_{23}$ hydrocarbon group, at least one of $R^1$, $R^2$, $R^3$, or $R^4$ is a moiety other than hydrogen, and $C^2$ is a carbon that on average is from 0 to about 15 percent primary;

(b) said values of m, n, w, x, y, and z are selected to provide suitable pharmaceutical carrier properties;

(c) said esterified alkoxylated polyol carrier is present in an amount sufficient to impart suitable body or coverage to said formulation;

(d) said esterified alkoxylated polyol carrier is substantially dermally non-allergenic, non-irritating, and non-digestible, and non-toxic; and (e) said pharmaceutical formulation is characterized by the absence of a foodstuff.

2. The pharmaceutical formulation of claim 1 wherein the esterified alkoxylated polyol carrier has an average value of $[(m\cdot z)+(n\cdot y)]$ in the range of from 0 to about 15.

3. The pharmaceutical formulation of claim 1 wherein the P organic radical of the esterified alkoxylated polyol is derived from a polyol selected from the group consisting of diols, triols, tetrols, saccharides, sugar alcohols, and mixtures thereof.

4. The pharmaceutical formulation of claim 1 wherein the P organic radical of the esterified alkoxylated polyol is derived from a triol selected from the group consisting of glycerin, trimethylol propane, trihydroxyhexane, trihydroxypentane, and mixtures thereof.

5. The pharmaceutical formulation of claim 1 wherein the P organic radical of the esterified alkoxylated polyol carrier is derived from a saccharide selected from the group consisting of glucose, fructose, mannose, galactose, arabinose, xylose, sorbitol, sorbose, sucrose, and mixtures thereof.

6. The pharmaceutical formulation of claim 1 wherein the P organic radical of the esterified alkoxylated polyol is derived from a sugar alcohol of formula $HOCH_2(CHOH)_nCH_2OH$, where $n=2-6$.

7. The pharmaceutical formulation of claim 1 wherein the

group of the esterified alkoxylated polyol carrier is derived from a fatty acid selected from the group consisting of caprylic acid, capric acid, lauric acid, myristic acid, myristoleic acid, stearic acid, palmitic acid, palmitoleic acid, ricinoleic acid, linoleic acid, linolenic acid, elaeostearic acid, arachidic acid, behenic acid, erucic acid, oleic acid, heptadecanoic acid, and mixtures thereof.

8. The pharmaceutical formulation of claim 1 wherein the esterified alkoxylated polyol carrier has an average value of $$\frac{x+y}{w+x+y+z}$$

in the range of from 0 to about 0.05.

9. The pharmaceutical formulation of claim 1 wherein B in the esterified alkoxylated polyol is a $C_{13}$-$C_{21}$ hydrocarbon group.

10. The pharmaceutical formulation of claim 1 wherein A in the esterified alkoxylated polyol is an oxyalkylene group derived from an epoxide selected from the group consisting of propylene oxide, 1,2-butylene oxide, isobutylene oxide, 2,3-butylene oxide, epichlorohydrin, allyl glycidyl ether, styrene oxide, phenyl glycidyl ether, 1,2-pentene oxide, tetramethyl ethylene oxide, trimethyl ethylene oxide, cyclohexene oxide, and mixtures thereof.

11. The pharmaceutical formulation of claim 1 wherein only one of $R^1$, $R^2$, $R^3$, or $R^4$ in the esterified alkoxylated polyol carrier is a moiety other than hydrogen.

12. The pharmaceutical formulation of claim 1 wherein P in the esterified alkoxylated polyol carrier is glyceryl.

13. The pharmaceutical formulation of claim 1 wherein the sum of $w+x+y+z$ in the esterified alkoxylated polyol carrier is about 3.

14. The pharmaceutical formulation of claim 1 wherein A in the esterified alkoxylated polyol carrier is an oxypropylene unit.

15. The pharmaceutical formulation of claim 1 wherein P is glyceryl, the sum of $w+x+y+z$ is about 3, A is an oxypropylene unit, B is a $C_{13}$-$C_{21}$ hydrocarbon group, the average value of $[(m \cdot z)+(n \cdot y)]$ is in the range of from 0 to about 15, and only one of $R^1$, $R^2$, $R^3$, or $R^4$ is a moiety other than hydrogen.

16. The pharmaceutical formulation of claim 1 wherein the sum of $w+x+y+z$ is about 3, B is a $C_{13}$-$C_{21}$ hydrocarbon group, and the average value of $[(m\ z)+(n\ y)]$ is in the range of from 0 to about 15.

17. The pharmaceutical formulation of claim 1 wherein on average $C^2$ is from 0 to about 5 percent primary.

18. A method of administering a medication ingredient which comprises treating an animal or human subject with the pharmaceutical formulation of claim 1.

19. An improved pharmaceutical formulation comprising an effective amount of a medication ingredient in admixture with an esterified propoxylated glycerol carrier of formula $$[BCO]_w\text{—}\overset{\underset{\displaystyle [OH]_x}{|}}{P}\text{—}[\text{O—}(A)_n\text{—}C^1R^1R^2\text{—}C^2R^3R^4\text{—}OH]_y$$
$$[O\text{—}(A)_m\text{—}C^1R^1R^2\text{—}C^2R^3R^4\text{—}OCB]_z$$

wherein
(a) P is a glyceryl radical, the sum of $w+x+y+z$ is about 3, $$\frac{x+y}{w+x+y+z}$$

is an average number less than about 0.15, z is an average number in the range of about 2 to 3, A is an oxypropylene unit, the average value of $[(m \cdot z)+(n \cdot y)]$ is in the range from 0 to about 15, B is a $C_{11}$-$C_{21}$ hydrocarbon group, one only of $R^1$, $R^2$, $R^3$, and $R^4$ is methyl with the other R groups being hydrogen, and $C^2$ is a carbon that on average is from 0 to about 5 percent primary;

(b) said values of m, n, w, x, y, and z are selected to provide suitable pharmaceutical carrier properties;

(c) said esterified propoxylated glycerol carrier is present in an amount sufficient to impart suitable body or coverage to said formulation;

(d) said esterified propoxylated glycerol carrier is substantially dermally non-allergenic, non-irritating, non-digestible, and non-toxic; and (e) said pharmaceutical formulation is characterized by the absence of a foodstuff.

20. The pharmaceutical formulation of claim 19 wherein the esterified propoxylated glycerin carrier has an average value of $$\frac{x+y}{w+x+y+z}$$

in the range of from 0 to about 0.05.

21. The pharmaceutical formulation of claim 19 wherein the $$\overset{O}{\underset{\|}{BCO}}\text{—}$$

group of the esterified propoxylated glycerin carrier is derived from a fatty acid selected from the group consisting of caprylic, capric, lauric, myristic, myristoleic, stearic, palmitic, palmitoleic, rincinoleic, linoleic, linolenic, elaeostearic, arachidic, behenic, erucic, oleic, heptadecanoic acid, and mixtures thereof.

22. A method of administering a medication ingredient which comprises treating an animal or human with the pharmaceutical formulation of claim 19.

23. A method of rendering a medication ingredient suitable for administering to an animal or human subject having a lower gastrointestinal tract such that the medication ingredient is delivered to the lower gastrointestinal tract when said medication ingredient is ingested orally, said method comprising incororating the medication ingredient into a pharmaceutical formulation comprised of the medication ingredient and an effective amount of an esterified alkoxylated polyol carrier of formula $$[BCO]_w\text{—}\overset{\underset{\displaystyle [OH]_x}{|}}{P}\text{—}[\text{O—}(A)_n\text{—}C^1R^1R^2\text{—}C^2R^3R^4\text{—}OH]_y$$
$$[O\text{—}(A)_m\text{—}C^1R^1R^2\text{—}C^2R^3R^4\text{—}OCB]_z$$

wherein
(a) P is an organic radcial derived from a polyol, the sum of $w+x+y+z$ is from 2 to 8, $$\frac{x+y}{w+x+y+z}$$

on an average number in the range of from 0 to about 0.15, z is an average number in the range of from about 2 to the sum of $w+x+y+z$, A is an oxyalkylene unit having at least 3 carbon atoms, B is a $C_7$-$C_{23}$ hydrocarbon group, at least one of $R^1$, $R^2$, $R^3$, or $R^4$ is a moiety other than hydrogen, and $C^2$ is a carbon that on average is from 0 to about 15 percent primary;

(b) said values of m, n, w, x, y, and z are selected to provide suitable pharmaceutical carrier properties; and (c) said esterified alkoxylated polyol carrier is substantially non-digestible and non-toxic; wherein said pharmaceuticla formulation is characterized bythe absence of a foodstuff.

24. A method of rendering a medication ingredient suitable for administering to an animal or human subject having a lower gastrointestinal tract such that the medication ingredient is delivered to the lower gastrointestinal tract when said medication ingredient is ingested orally, said method comprising incorporating the medication ingredient into a pharmaceutical formulation comprised of the medication ingredient and an effective amount of an esterified propoxylated glycerol carrier of formula

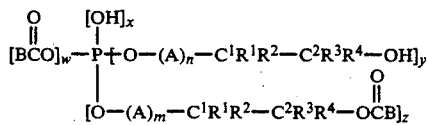

wherein (a) P is a glyceryl radicla, the sum of $w+x+y+z$ is about 3, $$\frac{x+y}{w+x+y+z}$$

is an average number less than about 0.15, z is an average number in the range of from about 2 to 3, A is an oxypropylene unit, the average value of $[(m \cdot z)+(n \cdot y)]$ is in the range from 0 to about 15, B is a $C_1$-$C_{21}$ hydrocarbon group, one only of $R^1$, $R^2$, $R^3$, and $R^4$ is methyl with the other R groups being hydrogen, and $C^2$ is a carbon that on average is from 0 to about 5 percent primary;

(b) said values of m, n, w, x, y, and z are selected to provide suitable pharmaceutical carrier properties; and (c) said esterified propoxylated glycerol carrier is substantially non-digestible and non-toxic; wherein said pharmaceutical formulation is characterized by the absence of a foodstuff.

* * * * *